United States Patent [19]

Tong

[11] 4,352,356
[45] Oct. 5, 1982

[54] URINARY INCONTINENCE GARMENT

[75] Inventor: David P. Tong, Nuneaton, England

[73] Assignee: Humanicare International Inc., East Brunswick, N.J.

[21] Appl. No.: 205,105

[22] Filed: Nov. 10, 1980

[30] Foreign Application Priority Data

Jan. 25, 1980 [GB] United Kingdom ............... 8002635

[51] Int. Cl.³ ............................................ A61F 13/16
[52] U.S. Cl. .................................. 128/288; 66/177; 128/295
[58] Field of Search .................. 128/288, 295; 66/177

[56] References Cited

U.S. PATENT DOCUMENTS

| | | |
|---|---|---|
| 1,580,464 | 4/1926 | Blumenfeld . |
| 2,062,978 | 12/1936 | King . |
| 2,583,553 | 1/1952 | Faure . |
| 2,627,858 | 2/1953 | Miller . |
| 2,654,367 | 10/1953 | Turnham . |
| 2,699,170 | 1/1955 | Morin . |
| 2,706,389 | 4/1955 | Garrou et al. ............... 128/288 |
| 2,839,057 | 6/1958 | Argyll . |
| 3,315,676 | 4/1967 | Cooper . |
| 3,344,789 | 10/1967 | Arnold et al. . |
| 3,452,753 | 1/1969 | Sanford . |
| 3,489,149 | 1/1970 | Larson ......................... 128/288 |
| 3,613,686 | 10/1971 | DeWoskin ................... 128/288 |
| 3,707,969 | 1/1973 | Sanford . |
| 3,760,611 | 9/1973 | Duckworth ................... 66/177 |
| 3,916,901 | 11/1975 | Korgemets . |
| 3,938,522 | 2/1976 | Repke . |
| 4,005,712 | 2/1977 | Karami . |
| 4,018,226 | 4/1977 | Korgemets . |
| 4,040,423 | 8/1977 | Jones, Sr. . |
| 4,244,367 | 1/1981 | Rollenhagen .................. 128/288 |

FOREIGN PATENT DOCUMENTS

| | | | |
|---|---|---|---|
| 1074501 | 1/1980 | Canada ......................... | 128/288 |
| 1411087 | 10/1975 | United Kingdom ........... | 128/288 |

Primary Examiner—C. Fred Rosenbaum
Attorney, Agent, or Firm—James & Franklin

[57] ABSTRACT

The garment has a body portion with an internal pouch which is adapted to receive an absorbent pad. The pouch is formed of a liquid impervious panel situated adjacent to the body portion and a liquid penetrable panel secured along its sides to the body portion. The sides of the liquid impervious panel extend from the body portion toward the liquid penetrable panel, to which same are attached, so as to form a liquid retention barrier along the sides of the pouch. The body portion is formed of a knitted fabric including interlocked courses of a staple fiber yarn and of a bulked continuous filament yarn. The liquid impervious panel includes a knitted fabric coated with polyurethane. The liquid penetrable panel comprises a polyester yarn knitted into a fabric with a semi-cardigan stitch.

35 Claims, 5 Drawing Figures

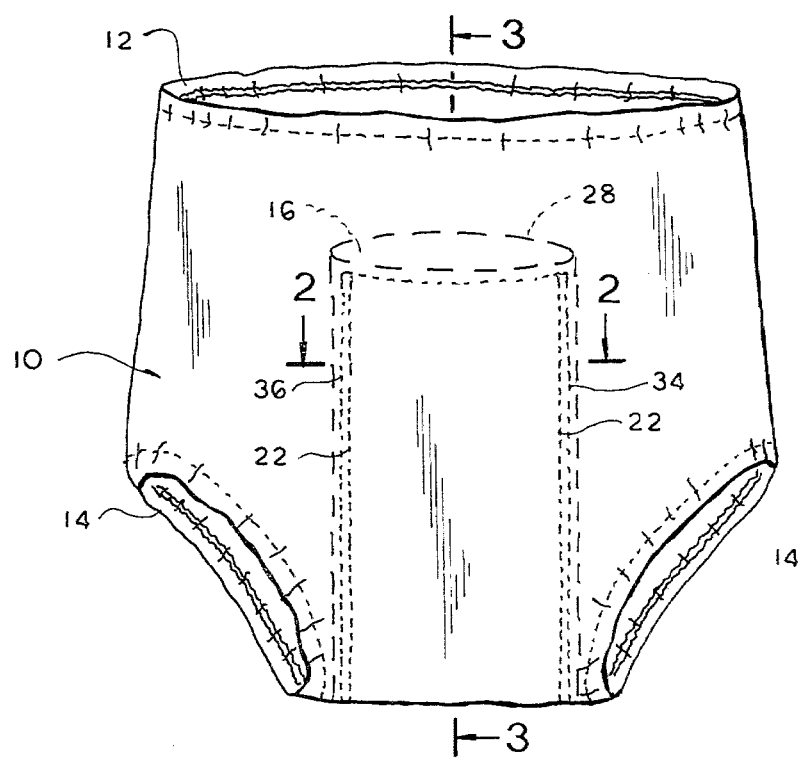
FIG. I
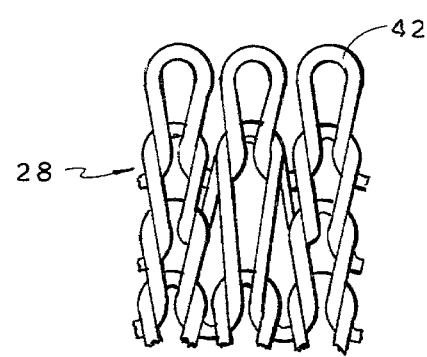
FIG. 5

URINARY INCONTINENCE GARMENT

BACKGROUND OF THE INVENTION

The present invention relates to urinary incontinence garments and, more particularly, to a unique construction for same and to the construction of an internally situated absorbent pad receiving pouch therein.

It is estimated that, in the United States today, literally millions of adult men and women suffer from urinary incontinence. This condition often leads to inconvenience, awkwardness and embarrassment, with the result that individuals with this problem may curtail their normal activities to avoid detection. To permit such individuals to lead a more normal life, garments designed with urine absorbing capacity are used.

Many different types and designs of garments have been tried. However, in each instance, the garment employed has unacceptable or unpleasant disadvantages, making same less than desirable. Plasticized or rubberized briefs have been used, but have been found to be hot, damp and uncomfortable. Pants made out of paper have also been used, but are objectable to because of the rustling sound and the soreness and chaffing which garments of this construction often cause. Even infant disposable diapers, cut apart and taped to fit, have been tried, but unsuccessfully.

Without doubt, the most important single function of a urinary incontinence garment is to safely and effectively manage urinary incontinence so as to insure that the wearer will not be embarrassed in public. Thus, the primary design objective of the garment is that same function dependably so as to give the wearer confidence to go about his or her daily routine unimpeded.

However, the garment also must be comfortable to wear and, at the same time, be able to be worn discretely so that there are no bulges or other telltale outlines visible when the garment is worn under conventional clothing. Thus, the garment must also always feel comfortable to the wearer, not hot or damp, and it must have the sufficient stretch capability to conform to the wearer's body. It should look and feel soft, not be bulky or cumbersome and must not shift or bind as it is worn.

Further, the incontinence garment must be easy to use. It should be designed to be easy to put on or take off, either by the wearer himself or by one caring for the wearer, in the event that the wearer is ill or senile. In addition, the liquid absorbent portion, generally in the form of a pad, must be easily inserted and removed from the pant in a manner which prevents the hands from touching the wet sections thereof.

The garment must also be easy to launder and, preferably, washable by hand or machine, using conventional detergents. The garment should dry quickly and maintain its shape and neat fit after repeated launderings.

The present invention meets the above criteria by employing a unique construction and specially designed fabrics for the body portion of the garment, as well as for the internally situated pouch into which the absorbent pad is received. The pouch is constructed of a liquid impervious panel adjacent the body portion and a liquid penetrable panel secured along its sides to the body portion. A liquid retention barrier along the sides of the pouch acts to prevent liquid seepage until the liquid can be absorbed by the pad.

It is, therefore, a prime object of the present invention to provide a urinary incontinence garment which is comfortable to wear, being composed of a lightweight knit fabric which is aesthetically pleasing, as well as soft to the touch, and which permits air to penetrate through so that the garment does not feel hot or damp.

It is another object of the present invention to provide a urinary incontinence garment which is highly effective due to the unique structure of the leak-proof pocket, such that it is dependable, providing the wearer with confidence and security.

It is another object of the present invention to provide a urinary incontinence garment which is discrete and, thus, not bulky, cumbersome or detectable, but which affords the wearer freedom to move about with ease.

It is another object of the present invention to provide a urinary incontinence garment which will fit well, retain its shape, not change position and is easy to use, permitting insertion and removal of the pad without removing the garment.

It is another object of the present invention to provide a urinary incontinence garment which is reusable such that the fabric washes easily, dries quickly and maintains its shape.

In accordance with the present invention, a urinary incontinence garment is provided having a body portion in the form of pants. A pouch is situated along the interior of the body portion and is adapted to receive an absorbent pad therein. The body portion comprises a knitted fabric. The knitted fabric is formed of interlocked courses of a staple fabric yarn and a bulked continuous filament yarn.

Thus, the body portion comprises alternate courses of different type yarns. Preferably, the alternate courses are regularly interposed with one another and have a one-to-one spacing so as to give the fabric an appearance of vertical ribbing and improve the breathability thereof.

The staple fabric yarn preferably comprises a spun polyester staple yarn or a polypropylene staple yarn, so as to give the garment a soft feel and the appearance of a conventional undergarment. The bulked continuous filament yarn provides the garment with elasticity and improved shape recovery during wear and after washing to insure that the garment maintains a close fit to the body—essential for the prevention of leaks.

The pouch comprises a liquid penetrable panel and a liquid impervious panel. The latter has a first portion situated adjacent the body portion and a second portion extending from the first portion toward the interior of the garment and being affixed to the liquid penetrable panel.

The first portion comprises the central part of the liquid impervious panel and the second portion comprises the sides thereof. The sides are bent toward each other and then affixed to the liquid penetrable panel so as to form liquid retention barrier means along the sides of the pouch.

While the total absorbency of the pads used in the garment is adequate to absorb the normal amount of liquid, the rate of absorbency may be too slow to absorb a large amount of liquid in a short time period, thus causing seepage along the sides of the pad. In order to avoid seepage, the liquid must be retained for a time sufficient to permit the pad to absorb all of the liquid. The liquid retention barrier means created along the sides of the pouch is designed to retain liquid within the pouch until all of the liquid can be absorbed by the pad.

The liquid impervious panel preferably comprises a knitted fabric coated with polyurethane. The knitted fabric itself is preferably nylon or polyester and is preferably transfer coated with a sheet of polyurethane. Such a fabric does not contain a plasticizer and, therefore, cannot harden after washing.

The liquid penetrable panel comprises a knitted fabric composed of polyester yarn. Preferably, the polyester yarn is knitted in a semi-cardigan stitch. The polyester gives the liquid penetrable panel the softness required for this portion of the garment while having minimal liquid absorption characteristics. The semi-cardigan knit results in an open fabric, permitting the maximum possible rate of penetration of liquid.

To these and such other objects which may hereinafter appear, the present invention relates to a urinary incontinence garment as described in detail in the following specification and recited in the annexed claims, taken together with the accompanying drawings, wherein like numerals refer to like parts, and in which:

FIG. 1 is a front view of the incontinence garment of the present invention;

FIG. 5 is an enlarged, idealized fragmentary view of the liquid penetrable fabric showing the knitted structure thereof.

Figure 3:
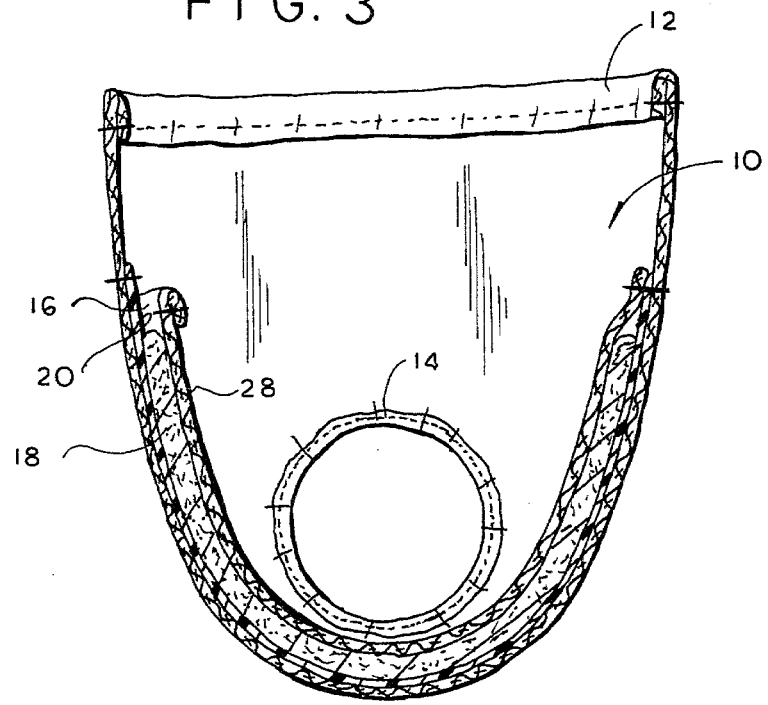
FIG. 3 is a cross-sectional view of the garment of the present invention, taken along line 3—3 of FIG. 1.

As seen in FIGS. 1 and 3, the urinary incontinence garment of the present invention comprises a body portion 10 in the form of a brief or pant. Portion 10 is provided with a stretchable waistband 12 and stretchable leg openings 14 which are formed by folding the fabric of body portion 10 over, so as to provide a channel for an elastic band or the like. A tab (not shown) may extend from each elastic band so as to permit the effective lengths of same to be individually adjustable.

Figure 2:
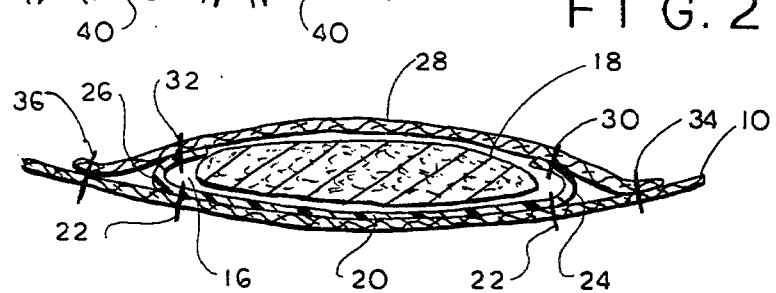
FIG. 2 is a cross-sectional view, taken along line 2—2 of FIG. 1, showing the construction of the pouch.

Within the interior of the garment is provided a pouch 16 designed to receive a high absorbency pad 18 therein. The construction of pouch 16 is best appreciated with reference to FIG. 2. A liquid impervious panel 20 has a first, central portion situated adjacent to the interior of the fabric of body portion 10 and is affixed thereto along lines 22. A second portion, in the form of the sides of the liquid impervious panel 20, extend beyond lines 22 towards the interior of the garment so as to form flaps 24, 26. Flaps 24, 26 are bent towards each other and affixed at 30, 32, respectively, to a liquid penetrable panel 28 which forms the interior wall of the pouch. Panel 28 is affixed at its sides 34, 36 to body portion 10. A high absorbency pad 18 is inserted through the top of pouch 16, which remains open. The other end of pouch 16 is closed to assure proper positioning of the pad 18.

In this manner, the sides of pad 18 are enclosed by liquid retention barriers formed by portions 24 and 26 of liquid impervious panel 20. Normally, when incontinence occurs, a relatively large amount of liquid is released during a short period of time. While pad 18 is designed to absorb all of the liquid which is released, the rate of absorbency of pad 18 may be insufficient to prevent momentary leakage of the liquid out of the sides of the pad and, thus, the pouch, which would result in an embarrassing wetness on the exterior of the garment on either side of the pouch. To prevent this, and, thus, give the absorbent pad 18 sufficient time to absorb the liquid which is released, flaps 24, 26 of the liquid impervious panel are extended inwardly towards the interior of the garment, bent towards each other, and then affixed to liquid penetrable panel 28 so as to form liquid retention barriers along the sides of the pouch. These barriers prevent the liquid from migrating from within the pouch to the exterior of the garment for a time sufficient for pad 18 to absorb same.

The structure of the fabric from which the body portion 10 is manufactured is of great importance is insuring the proper appearance, softness, breathability and shape retention of the garment. The fabric is a knitted interlock fabric consisting of courses of a staple fiber yarn 38 and courses of a bulked continuous filament yarn 40 regularly interspaced with one another. Preferably, the different types of yarn are utilized for alternate courses for the fabric, although different spacings may be employed, for example, one course of bulked yarn for every two or three of staple fiber yarn, or one of staple fiber yarn for every two or three of bulked yarn. However, it has been found that 1:1 spacing is especially advantageous as it results in a fabric with the appearance of vertical ribbing and improved breathability.

Any suitable yarns may be employed, including natural fiber or synthetic fiber yarns for the staple fiber yarns 38 and for the bulked yarn 40, any synthetic fiber which is capable of being bulked. A particularly useful combination comprises a spun polyester staple yarn (such as polyester cotton-spun yarn) and a bulked continuous filament polyester yarn. This fabric, especially with the different yarns used in alternate courses, is particularly suitable for use in incontinence garments, such as the present invention, which need to be comfortable and close fitting. However, polypropylene staple yarn may also be used and such fibers as mylon or cotton may be used for different fabrics.

The knitted interlocked fabric affords good shape recovery after wearing and washing, soft handle for comfort when in contact with the wearer's skin, and low moisture absorption. In addition, the fabric is resistant to laddering and piling.

Previously, it was common to fashion incontinence garments of fabrics comprising 100% polyester cotton-spun yarn which had the required soft feel and low absorbency characteristics. However, when the single 1:1 rib knit which has been used to give the required stretch characteristics, this fabric has poor stretch recovery characteristics and poor ladder resistance. It was attempted to improve the stretch recovery characteristics by using fabrics made entirely from bulked polyester yarns. However, while such fabrics have much improved shape retention characteristics, they are very harsh, have poor ladder resistance and are not generally acceptable for these reasons.

The fabric manufactured in accordance with the present invention, on the other hand, comprising a mixture of a staple fabric yarn 38 and a bulk continuous fabric yarn 40 in different courses, has all the attributes desired for the incontinence garments. Specifically, by the use of the appropriate combination of yarns, such a fabric can be produced which has much improved shape recovery after wearing and washing, as compared with the 100% polyester cotton-spun yarn fabric, the soft feel of a cotton-spun fabric, low absorption and high ladder resistance.

Figure 4:
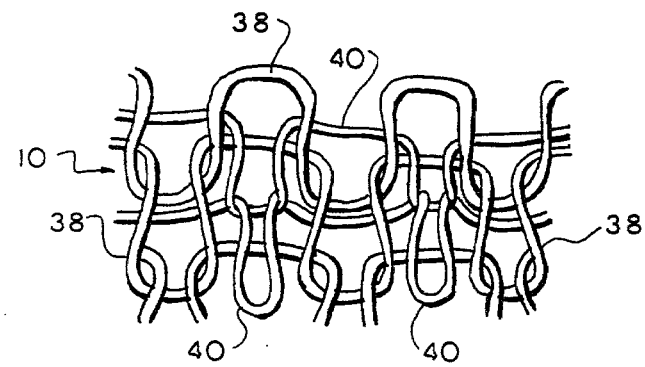
FIG. 4 is an enlarged, idealized fragmentary view of the fabric of the body portion of the garment showing the knitted structure thereof.

FIG. 4 shows an enlarged idealized fragmentary view of the interlocked fabric which is used in the body portion 10 of the urinary incontinence garment of the present invention. The fabric includes courses of staple fiber yarn 38 such as polyester cotton-spun yarn or the like, and courses of a bulked continuous filament yarn 40 such as a bulked continuous filament polyester yarn or the like. The courses are regularly interspaced with one another in a knitted interlock pattern, preferably utilizing a 1:1 spacing so as to provide the appearance of ribbing shown in FIG. 4.

After the knitting is performed as shown in FIG. 4, finishing is performed under tension-free conditions using a scour only. The temperatures, both in the finishing bath and the drying stages, are kept low in order to avoid setting the fabric. The body fabric should exhibit 100% stretch with full recovery after finishing.

FIG. 5 shows an idealized fragmentary view of the liquid penetrable fabric utilized in panel 28. This fabric is knitted from 100% spun polyester yarn 42. This yarn results in the softness required for this part of the garment but has substantially no water absorption. The type of knit used to produce panel 28 is known as either semi-cardigan or Swiss knit. The object of this knitting system is to give a very open fabric to allow the maximum possible rate of penetration of liquid. The semi-cardigan fabric 42 is fabricated on a knitting machine with a tuck stitch attachment. High setting temperatures may be utilized in the finishing of this fabric.

The liquid impervious panel 20 is made from either nylon or polyester yarn, preferably nylon 66, which is transfer coated with polyurethane. The resulting fabric is substantially water-proof, but does not contain a plasticizer such that it cannot harden after a period of washing.

It will now be appreciated that the present invention relates to certain novel structural features of a urinary incontinence garment and, in particular, to a novel fabric which is utilized to form the body portion of the garment and to the unique construction of the internal absorbent pad receiving pouch. The fabric which makes up the body portion of the garment includes alternate courses of a staple fiber yarn and of a bulked continuous filament yarn which are knitted in an interlock pattern with regular interspaces therebetween so as to form a fabric with the appearance of vertical ribbing, improved breathability, the necessary softness and elasticity, as well as enhanced shape retention characteristics.

The pad receiving pouch is formed on the interior of the body portion. The pouch consists of a liquid impervious panel, preferably made of nylon 66 with a polyurethane coating, which is situated adjacent the body fabric and has sides thereof which extend toward the interior of the garment and are bent toward each other. The sides of the liquid impervious panel are affixed to a liquid penetrable panel, preferably made of nylon or polyester yarn, knitted in a semi-cardigan pattern. In this manner, a pouch to receive a high absorbency pad having water retention barriers at either side thereof is formed.

The present invention is a urinary incontinence garment which affords the wearer the comfort of conventional undergarments and with maximum security due to the leak-proof design of the pouch. Because of the structure of the fabric of the body portion, the wearer has mobility. The garment is easy to use, maintains its excellent fit, stays in place. The garment is also reusable as it washes easily, dries quickly and retains its shape. Moreover, the garment is discrete in that it is not bulky or cumbersome and no tell-tale lines can be seen under clothing.

While only a single preferred embodiment of the present invention has been disclosed herein for purposes of illustration, it is obvious that many variations and modifications could be made thereto. It is intended to cover all of these variations and modifications which fall within the scope of the present invention, as defined by the following claims:

I claim:

1. A urinary incontinence garment in the form of a brief or the like comprising a body portion with leg openings and a pouch connected to the interior of said body portion extending between said leg openings, said pouch being adapted to receive an absorbent urinary incontinence pad therein, said body portion comprising a knitted fabric, said fabric comprising interlocked courses of a staple fiber yarn and of a bulked continuous filament yarn.

2. The garment of claim 1, wherein said courses of staple fiber yarn and bulked continuous filament yarn are regularly interspaced with one another.

3. The garment of claim 1, wherein said body portion comprises alternate courses of different type yarns.

4. The garment of claim 3, wherein said courses have a one-to-one spacing.

5. The garment of claim 1, wherein said staple fiber yarn comprises a spun polyester staple yarn.

6. The garment of claim 1, wherein said staple fiber yarn comprises a polypropylene staple yarn.

7. The garment of claim 1, wherein said pouch comprises a liquid penetrable panel and a liquid impervious panel having a first portion situated adjacent said body portion and a second portion extending from said first portion toward the interior of the garment and being affixed to said liquid penetrable panel.

8. The garment of claim 7, wherein said second portion comprises the sides of said liquid impervious panel and wherein said sides are bent toward each other.

9. The garment of claim 7, wherein the side of said liquid penetrable panel is affixed to said body portion.

10. The garment of claim 7, wherein said liquid impervious panel comprises a knitted fabric coated with polyurethane.

11. The garment of claim 7, wherein said liquid impervious panel comprises a knitted fabric comprising nylon fiber.

12. The garment of claim 7, wherein said liquid impervious panel comprises a knitted fabric comprising polyester fiber.

13. The garment of claim 11, wherein said nylon fiber comprises nylon 66.

14. The garment of claim 7, wherein said liquid penetrable panel comprises a knitted fabric comprising polyester yarn.

15. The garment of claim 14, wherein said polyester yarn is knitted in a semi-cardigan stitch.

16. The garment of claim 14, wherein said polyester yarn comprises 100% spun polyester.

17. A urinary incontinence garment in the form of a brief or the like comprising a body portion with leg openings and a pouch, connected to the interior of said body portion, said pouch extending between said leg openings, and comprising a liquid impervious panel, at least a portion of which is adjacent to said body portion, a liquid penetrable panel and liquid retention means, said liquid retention means extending along the side of said pouch.

18. The garment of claim 17, wherein said liquid impervious panel comprises a first portion situated adjacent said body portion and a second portion extending from said first portion toward the interior of the garment.

19. The garment of claim 18, wherein said second portion is affixed to said liquid penetrable panel.

20. The garment of claim 18, wherein the side of said liquid penetrable panel is affixed to said body portion.

21. The garment of claim 19, wherein said second portion comprises the sides of said liquid impervious panel and wherein said sides are bent toward each other.

22. The garment of claim 17, wherein said body portion comprises a knitted fabric, said fabric comprising interlocked courses of a staple fiber yarn and a bulked continuous filament yarn.

23. The garment of claim 22, wherein said courses of staple fiber yarn and bulked continuous filament yarn are regularly interspaced with one another.

24. The garment of claim 22, wherein said liquid impervious panel comprises a knitted fabric coated with polyurethane.

25. The garment of claim 22, wherein said liquid penetrable panel comprises a knitted fabric comprising polyester yarn.

26. The garment of claim 25, wherein said polyester yarn is knitted in a semi-cardigan stitch.

27. A urinary incontinence garment in the form of a brief or the like comprising a body portion including a front section and a rear section and leg openings, and a pouch connected to and extending along the interior surface of said body portion from approximately the middle of said front section, between said leg openings, to approximately the middle of said rear section, said pouch being adapted to accept a urinary incontinence liquid absorbent pad therein and comprising a liquid penetrable panel, a portion of which is spaced from said body portion, and a liquid impervious panel, at least a portion of which is situated adjacent the interior surface of said body portion.

28. The garment of claim 26, wherein said pouch further comprises a liquid retention means along the side thereof.

29. The garment of claim 26, wherein said pouch further comprises liquid retention means along the side thereof.

30. The garment of claim 29, wherein said liquid retention means comprises a portion of said liquid impervious panel.

31. The garment of claim 30, wherein said liquid retention means comprises a first part of said liquid impervious panel extending from said interior surface of said body portion and a second part of said liquid impervious panel extending from said first part inwardly towards the interior of said pouch.

32. The garment of claim 31, wherein said second part of said liquid impervious panel is retained in position by said liquid penetrable panel.

33. The garment of claim 31, wherein said second part of said liquid impervious panel is affixed to said liquid penetrable panel.

34. A urinary incontinence garment in the form of a brief or the like comprising a body portion with leg openings and a pouch connected to and extending along the interior of said body portion between said leg openings, said pouch being adapted to receive a urinary incontinence liquid absorbent pad therein, said pouch comprising liquid retention means situated along the side of said pouch and a liquid impervious panel.

35. The garment of claim 28, wherein said liquid retention means comprises a first part of said liquid impervious panel extending from said body portion and a second part of said liquid impervious panel extending from said first part toward the interior of said pouch.

* * * * *